United States Patent
Wang et al.

(10) Patent No.: US 10,093,881 B2
(45) Date of Patent: Oct. 9, 2018

(54) METHOD FOR VEGETABLE OIL DEACIDIFICATION BY ENZYMATIC AMIDATION

(71) Applicant: Jiangnan University, Wuxi (CN)

(72) Inventors: Xingguo Wang, Wuxi (CN); Xiaosan Wang, Wuxi (CN); Qingzhe Jin, Wuxi (CN); Jiyuan Lu, Wuxi (CN)

(73) Assignee: Jiangnan University, Wuxi, Jiangsu Province (CN)

( * ) Notice: Subject to any disclaimer, the term of this patent is extended or adjusted under 35 U.S.C. 154(b) by 0 days.

(21) Appl. No.: 15/269,288

(22) Filed: Sep. 19, 2016

(65) Prior Publication Data

US 2017/0158983 A1    Jun. 8, 2017

(30) Foreign Application Priority Data

Dec. 8, 2015    (CN) .......................... 2015 1 0916172

(51) Int. Cl.
| | |
|---|---|
| C11B 3/00 | (2006.01) |
| C12P 7/64 | (2006.01) |
| C12P 13/02 | (2006.01) |
| C11B 3/02 | (2006.01) |
| C11C 3/00 | (2006.01) |

(52) U.S. Cl.
CPC ................ *C11B 3/003* (2013.01); *C11B 3/02* (2013.01); *C11C 3/00* (2013.01); *C11C 3/003* (2013.01); *C12P 7/6445* (2013.01); *C12P 13/02* (2013.01)

(58) Field of Classification Search
None
See application file for complete search history.

(56) References Cited

FOREIGN PATENT DOCUMENTS

| CN | 1850947 | * | 10/2006 |
| CN | 104327954 | * | 2/2015 |
| CN | 104774686 | * | 7/2015 |

OTHER PUBLICATIONS

Prasanth et al. J Oleo Sci. 2014;63(12):1209-21. Epub Nov. 12, 2014. (Abstract).*
Wang et al. Guocheng Gongcheng Xuebao (2014), 14(4), 605-609 (Abstract).*
Bhattacharyya et al. European Journal of Lipid Science and Technology, vol. 91, Issue 1, pp. 27-30, 1989.*

* cited by examiner

*Primary Examiner* — Christian L Fronda
(74) *Attorney, Agent, or Firm* — IPro, PLLC; Na Xu

(57) ABSTRACT

The present invention provides a method for vegetable oil deacidification by enzymatic amidation, which relates to the field of oil refining technology. The present invention is carried out through mixing high acid value vegetable oil with ethanolamine at a certain molar ratio in a solvent or solvent-free system, adding with a certain amount of lipase, and reacting at certain temperature for a period of time. The monoethanolamine has been used as an acyl donor for the first time to react with free fatty acid, which avoids the increasing amount of by-products and great loss of neutral oil in reaction that involved with triglycerides. The method of the present invention has the advantages of high selectivity, high catalytic efficiency, and environment friendly in the reaction. From enzymes recycling, it greatly reduces costs, which shows tremendous potential in the application.

8 Claims, 3 Drawing Sheets

METHOD FOR VEGETABLE OIL DEACIDIFICATION BY ENZYMATIC AMIDATION

CROSS-REFERENCES AND RELATED APPLICATIONS

This application claims the benefit of priority to Chinese Application No. 201510916172.8, entitled "A method for vegetable oil deacidification by enzymatic amidation", filed Dec. 8, 2015, which is herein incorporated by reference in its entirety. Background of the Invention

FIELD OF THE INVENTION

The present invention relates to the field of oil refining technology, and more particularly relates to a method for vegetable oil deacidification by enzymatic amidation.

DESCRIPTION OF THE RELATED ART

It is usually low acid value in vegetable oil produced from common methods, while high acid value in oil produced under special condition of high moisture, improper storage or enzymes addition in process, among which high-acid value wheat germ oil and high-acid value rice bran oil are more typical. Oils possess high acid value mainly refer to the oil with acid value more than 20 mgKOH/g, among those rice bran oil is typical. It possesses reasonable acid composition and rich amount of oryzanol, squalene, VE (tocopherols, tocotrienols), sterols and other active substances, which is functional in improving immunity, lowering cholesterol, regulating blood lipids, and preventing atherosclerosis etc. It is an ideal edible oil and has been named as "nutritional and healthy oil" by nutritionists. Rice bran contains high lipase activity, leading to high content (generally more than 10%, some even between 30% to 40%) of free fatty acid in rice bran oil.

The traditional alkali refining process has many disadvantages such as large amounts of water and chemicals requirement, which leads to refining loss and nutritional quality declination; plenty of polluting wastewater generated in decarboxylation process that harmful to the environment, and the physical refining process with low refining rate and refining losses, combine with stringent requirements on equipment. With the development of biotechnology, the new enzymatic technology attracts the attention of scholars for its mild process and high catalytic efficiency. Lipase-catalyzed deacidification is generally implemented using low carbon alcohol, monoacylglycerols or phytostanols (alkyl) alcohol asacyl acceptors for esterification. When low carbon alcohol are used as acyl acceptors, it react with neutral oils triglyceride to produce byproducts like monoglycerides or diacylglycerol, which causes the loss of neutral oil. Besides, monoglycerides and glycerol are main precursors of hazardous substances glycidyl, and the whole reaction process is time-consuming.

Traditional deacidification process possesses disadvantages such as great loss of neutral oil, stringent requirements on crude oil pretreatment, or high energy consumption. While enzyme application can not only reduce nutrient loss, but also ensure oil quality in process of high acid value oil deacidification. It meanwhile overcomes the defects of rich amount of by-products and uncontrollable reaction condition in common esterification deacidification reaction.

DETAILED DESCRIPTION

The goal of the present invention is to provide a method of enzymatic deacidification with simple process and high refine rate, which overcomes the shortcomings of common methods for vegetable oil deacidification.

To solve the above technical problem, the present invention is carried out through following steps: mixing high acid value vegetable oil with ethanolamine in a certain molar ratio in a solvent or solvent-free system, adding certain amount of lipase, and reacting at certain condition; deacidified vegetable oil is obtained after reacting under a certain condition; wherein said molar ratio is 1: (1-3); quality of said lipase is 1~10% of total quality of high-value acid oil and monoethanolamine; and the condition is under 50~100° C. for 1~35 h.

In one embodiment, said solvent system comprises one or more compounds selected from a group consisting of hexane, petroleum ether, ethyl acetate, diethyl ether, acetone and a combination thereof.

In one embodiment, the ratio of high acid value vegetable oil quality with organic solvent volume is 1: (0.5-5) (g/ml).

In one embodiment, the system is solvent-free system; the reaction is under vacuum, the vacuum degree is between 0.075~0.1 Mpa.

In one embodiment, the lipase comprises one or mor immobilized enzymes selected from a group consisting of Lipozyme RM IM (250 IUN/g), Lipozyme 435 (8000 PLU/g), Lipozyme TL IM (275 IUN/g), Novozym 435 (10000 PLU/g) and a combination thereof.

The beneficial effects of the present invention:

(1) The enzymatic amidation present in the invention has following advantages: high selectivity, high catalytic efficiency, and less nutrient loss, which ensures the quality of the oil; the acid value can be reduced to 4 mg KOH/g or less, which meets the needs of high acid value oil deacidification.

(2) The present invention uses monoethanolamine as an acyl donor to react with free fatty acid, which avoids the lot of by-products and great neutral oil loss in production from reacting with triglycerides.

(3) The process of the present invention is carried out under mild and environmental conditions with low energy consumption; the recycling enzyme, zeolite, and organic solvent greatly reduce the cost and has tremendous potential.

EXAMPLES

Materials and Methods

To make features and advantages of the present invention more comprehensible, the following specific embodiments of the present invention will be described in detail.

There are numerous specific details set forth in the following description, in order to understand the present invention fully, but the present invention can also be used in other ways different from the follow embodiments described here, one skilled in the art can do similarly promotion without departing from the connotation of the invention, therefore the present invention is not limited by the following specific embodiments disclosed.

Next, "one embodiment" or "an embodiment" herein called means particular feature, structure, or characteristics that contained in at least one implementation of the present invention. That"in one embodiment" present in various places in specification does not refer to the same embodiment, Nor does it mean a separate or alternative embodiments exclusive with other example embodiments mutually.

Example 1

Figure 1:
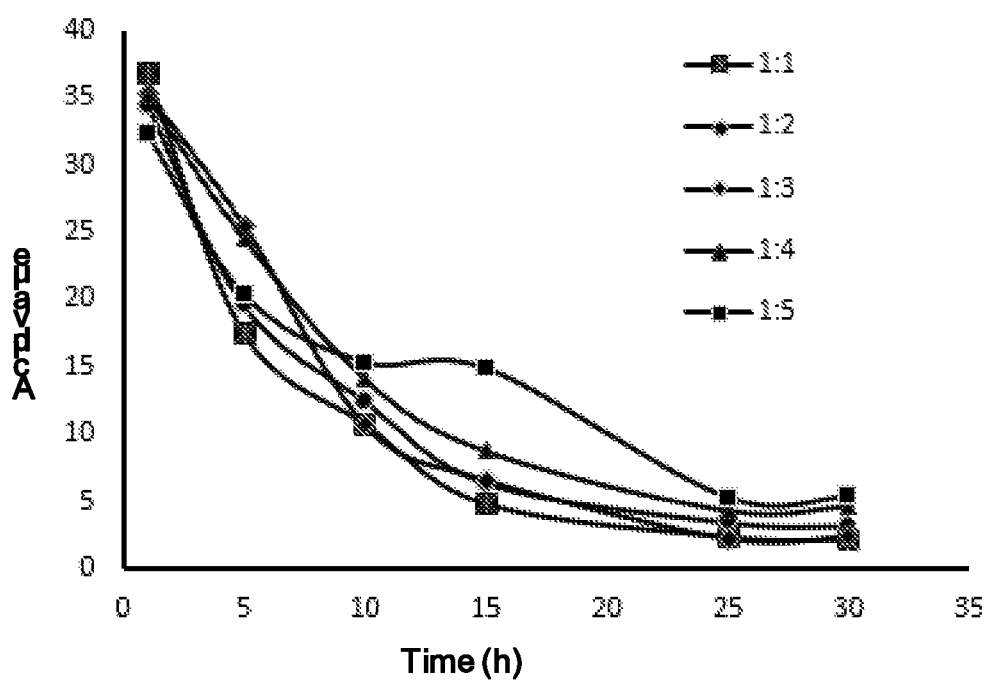
FIG. 1 is the effect of enzymatic deacidification of high acid value rice bran oil under reaction condition of different substrate ratio.

Intermittent enzyme reaction was carried out in a batch stirred tank reactor, the free fatty acids and ethanolamine was mixed at a molar ratio of 1:1-5 (acid value of high acid rice bran oil is 40.8 mg KOH/g), the high acid value vegetable oil mixing with hexane at 1:2 (w/v), 5% molecular sieves of 4 A and 4% immobilized lipase Lipozyme 435 was added. The system was stirred at 90° C. under normal pressure for a certain time, and then centrifuged under 4000 r/min for 10 min to remove molecular sieve, fatty acid monoethanolamine and unreacted monoethanolamine Subsequently rotary evaporation was used to evaporate hexane under 0.085 Mpa, at 75° C. The vegetable oil possessed low acid value (according to GB 5530-85, the same as below) was harvest in hexane that been condensed in the condenser. It can be seen in FIG. 1, with the increase of time, the acid value of oil reduced, and the deacidification effect enhanced, with the increasing molar ratio of monoethanolamine with free fatty acids, little changes appeared on deacidification effect. The acid value was below 2 in oil that produced under a 30 h reaction with 1:1 molar ratio of monoethanolamine and free fatty acids. Thus, the 1:1 substrate molar ratio is preferred according to the purely economic perspective.

Example 2

Figure 2:
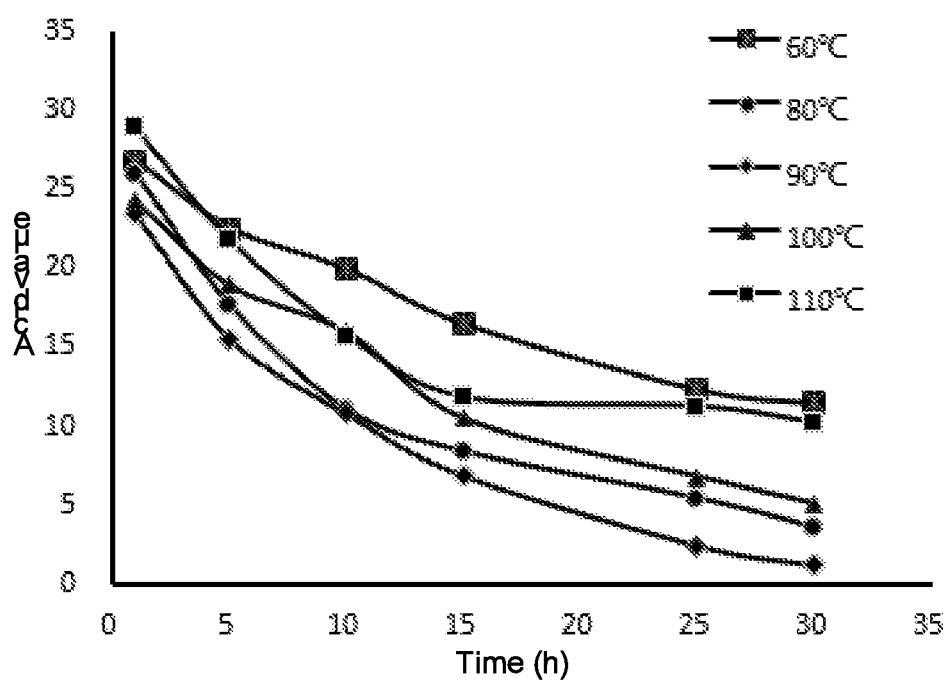
FIG. 2 is the effect of enzymatic deacidification of high acid value rice bran oil under reaction condition of different temperature.

Intermittent enzyme reaction was carried out in a batch stirred tank reactor, the free fatty acids and ethanolamine was mixed at a molar ratio of 1:1 (acid value of high acid rice bran oil is 34.5 mg KOH/g), the high acid value vegetable oil mixing with petroleum ether at 1:2 (w/v), 5% molecular sieves of 4 A, and 6% immobilized lipase of Lipozyme TL IM was added, the system was stirred at different temperatures under normal pressure for a certain time, and then centrifuged under 4000 r/min for 10 min to remove the lipase, molecular sieve, fatty acid monoethanolamine and unreacted monoethanolaminen, subsequently rotary evaporation was used to evaporate petroleum ether under 0.085 Mpa at 75° C. The vegetable prossessed low acid value was harvest in petroleum ether that been condensed in the condenser. It can be seen in FIG. 2, with the increase of time the acid value of oil reduced, and the deacidification effect was enhanced. The reaction temperature significantly influenced the efficient of deacidification. With the increasing of temperature, effect of deacidification enhanced. As shown in FIG. 2, the effect of de-acidification turned worse when temperature was above 90° C.

Example 3

Figure 3:
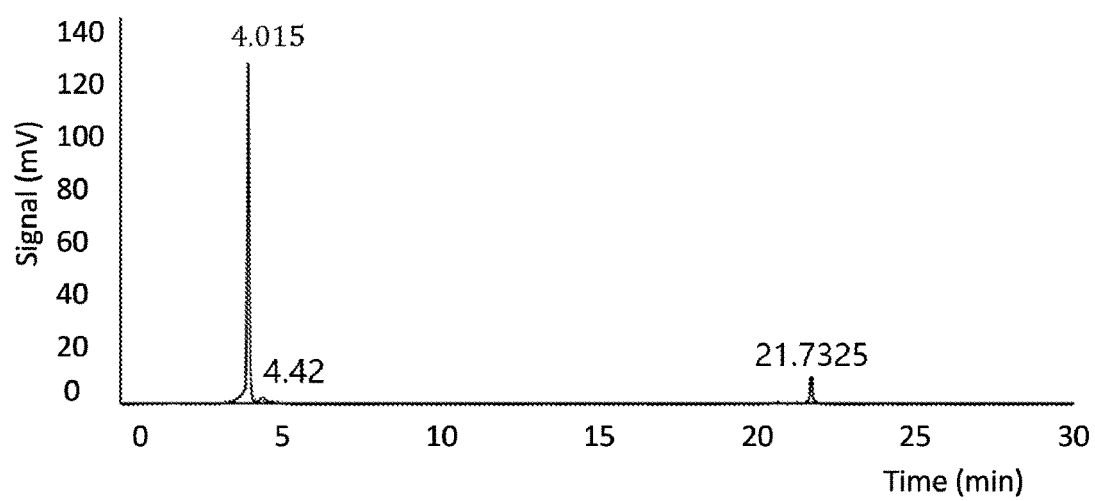
FIG. 3 is the HPLC chromatogram of reaction product from enzymatic deacidification.

Intermittent enzyme reaction was carried out in a batch stirred tank reactor, the free fatty acids and ethanolamine was mixed at a molar ratio of 1:1 (acid value of high acid rice bran oil is 31.8 mg KOH/g), the high acid value vegetable oil mixing with ethyl acetate at 1:3 (w/v), 5% molecular sieves of 4 A, and 6% immobilized lipase of Lipozyme RM IM was added, The system was stirred at 60° C. for 20 h under normal pressure, and then centrifuged at 4000 r/min for 10 min to remove the lipase, molecular sieve, fatty acid monoethanolamine and unreacted monoethanolamine After that, rotary evaporator was used to evaporate the ethyl acetate under 0.085 Mpa at 75° C. The vegetable oil possessed low acid value (3.05 mg KOH/g) was harvest in ethyl acetate that been condensed in the condense. The normal phase HPLC chromatogram of the reaction product is shown in FIG. 3, the wherein retention time at 4.015 min, 4.42 min and 21.7325 min was rice bran oil triglycerides, fatty acids and fatty acid amide product ethanol separately. Monoglycerides, diacylglycerol and other by-products had not been found in HPLC determination.

Example 4

Intermittent enzyme reaction was carried out in a batch stirred tank reactor, free fatty acids and ethanolamine was mixed at a molar ratio of 1:1 (acid value of high acid rice bran oil is 30.4 mg KOH/g), the high acid value vegetable oil mixing with hexane at 1:1.5 (w/v), 5% molecular sieves of 4 A, and 5% Lipozyme 435 of immobilized lipase was added. The system was stirred at 90° C. for 2 h under normal pressure, and then centrifuged at 4000 r/min for 10 min to remove, the lipase, molecular sieve, fatty acid monoethanolamine and unreacted monoethanolamine, subsequently the rotary evaporator was used to evaporate hexane under 0.085 Mpa at 75° C. The vegetable oil possessed low acid value (1.05 mg KOH/g) was harvest in hexane that been condensed in the condenser.

Example 5

Intermittent enzyme reaction was carried out in a batch stirred tank reactor, free fatty acids and ethanolamine was mixed at a molar ratio of 1:2 (acid value of high acid rice bran oil is 46.8 mg KOH/g), the high acid value vegetable oil mixing with petroleum ether at 1:2 (w/v), 5% molecular sieves of 4 A, and 8% Novozym 435 of immobilized lipase was added. The reaction system was stirred at 80° C. for 10 h under normal pressure, and then centrifuged at 4000 r/min for 10 min to remove the lipase, molecular sieve, fatty acid monoethanolamine and unreacted monoethanolamine, subsequently the rotary evaporator was used to evaporate the petroleum ether under 0.085 Mpa at 75° C. The vegetable oil possessed low acid value (2.65 mgKOH/g) was harvest in petroleum ether that been condensed in the condenser.

Example 6

Intermittent enzyme reaction was carried out in a batch stirred tank reactor, free fatty acids and ethanolamine was mixed at a molar ratio 1:0.5 (acid value of high acid rice bran oil is 25.6 mg KOH/g), the high acid value vegetable oil mixing with acetone at 1:3 (w/v), 5% molecular sieves of 4 A, and 10% Lipozyme RM IM of immobilized lipase was added. The reaction was stirred at 70° C. for 30 h under normal pressure, and then centrifuged at 4000 r/min for 10 min to remove the lipase, molecular sieve, fatty acid monoethanolamine and unreacted monoethanolamine, subsequently the rotary evaporator was used to evaporate the acetone under 0.085 Mpa at 75° C. The vegetable oil possessed low acid value (7.85 mgKOH/g) was harvest in acetone that been condensed in the condenser.

Example 7

Intermittent enzyme reaction was carried out in a batch stirred tank reactor, free fatty acids and ethanolamine was mixed at a molar ratio of 1:2 (acid value of high acid rice bran oil is 35.8 mg KOH/g), added with 5% Lipozyme 435 of immobilized lipase. The reaction system was stirred at 80° C. for 5 h, and then centrifuged at 4000 r/min for 10 min to remove the lipase, molecular sieve, fatty acid monoethanolamine and unreacted monoethanolamine, and the vegetable oil possessing low acid value (2.75 mgKOH/g) was obtained.

It can be seen that the monoethanolamine in the present invention was used as an acyl donor for the first time to react with free fatty acid, which avoids the byproducts and neutral oil loss in reaction with triglycerides. The method of the present invention has the advantages of high selectivity, high catalytic efficiency, and environment friendly in the reaction. From enzymes recycling, it greatly reduces costs, which shows tremendous potential in the application.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for vegetable oil deacidification by enzymatic amidation, wherein said method comprises mixing high acid value vegetable oil with monoethanolamine at a certain molar ratio in a solvent or solvent-free system, adding with a certain amount of lipase, and reacting at a certain condition; wherein said molar ratio of free fatty acids of said vegetable oil to said monoethanolamine is 1: (1 to 3); wherein the quality of said lipase is 1 to ≃10% of total quality of said vegetable oil and said monoethanolamine; and wherein said condition is at 50 to ≃100° C. for 1 to ≃35 h.

2. The method of claim 1, wherein said solvent system comprises one or more compounds selected from a group consisting of hexane, petroleum ether, ethyl acetate, diethyl ether, acetonein and a combination thereof.

3. The method of claim 2, the high acid value vegetable oil and organic solvent is at a ratio of 1: (0.5 to −5) (g/mL).

4. The method of claim 1, wherein said system is solvent-free system, and the reaction is under −0.075 to ≃0.1 Mpa.

5. The method of claim 1, wherein said lipase comprises one or more from a group consisting of Lipozyme RM IM immobilized enzyme, Lipozyme 435 immobilized enzyme, Lipozyme TL IM immobilized enzyme, Novozym 435 immobilized enzyme, and a combination thereof.

6. The method of claim 2, wherein said lipase comprises one or more from a group consisting of Lipozyme RM IM immobilized enzyme, Lipozyme 435 immobilized enzyme, Lipozyme TL IM immobilized enzyme, Novozym 435 immobilized enzyme, and a combination thereof.

7. The method of claim 3, wherein said lipase comprises one or more from a group consisting of Lipozyme RM IM immobilized enzyme, Lipozyme 435 immobilized enzyme, Lipozyme TL IM immobilized enzyme, Novozym 435 immobilized enzyme, and a combination thereof.

8. The method of claim 4, wherein said lipase comprises one or more from a group consisting of Lipozyme RM IM immobilized enzyme, Lipozyme 435 immobilized enzyme, Lipozyme TL IM immobilized enzyme, Novozym 435 immobilized enzyme, and a combination thereof.

* * * * *